US00PP18391P3

(12) United States Plant Patent
Hofstede et al.

(10) Patent No.: US PP18,391 P3
(45) Date of Patent: Jan. 1, 2008

(54) ***HYDRANGEA* PLANT NAMED 'HOPCORN'**

(50) Latin Name: *Hydrangea macrophylla*
Varietal Denomination: Hopcorn

(76) Inventors: Jacobus Gerardus Hofstede, Doormanstraat 6, Huissen (NL), 6852 AK; Wilhelmus Jacobus Gerardus Hofstede, Doormanstraat 6, Huissen (NL), 6852 AK ( * ) Notice: Subject to any disclaimer, the term of this patent is extended or adjusted under 35 U.S.C. 154(b) by 0 days.

(21) Appl. No.: 11/349,678

(22) Filed: Feb. 8, 2006

(65) Prior Publication Data

US 2007/0186319 P1 Aug. 9, 2007

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent Bell
(74) *Attorney, Agent, or Firm*—Jondle & Associates, P.C.

(57) ABSTRACT

A *hydrangea* cultivar particularly distinguished by its bright pink inflorescences with cupped sepals, dark green leaves, and vigorous growth habit is disclosed.

2 Drawing Sheets

Genus and species: *Hydrangea macrophylla.*
Variety denomination: 'Hopcorn'.

BACKGROUND OF THE NEW PLANT

The present invention comprises a new and distinct cultivar of *hydrangea,* botanically known as *Hydrangea macrophylla,* and hereinafter referred to by the cultivar name 'Hopcorn'. The new cultivar originated from a naturally occurring branch mutation of the parent *hydrangea* cultivar 'Mathilde Gutges' (unpatented) found in 1998 in Huissen, The Netherlands. The flowers of the mutant plant had smaller sepals and each sepal was cupped, unlike the normal flat sepals of the mutation parent plant.

Like the mutation parent, 'Hopcorn' has pink flowers which can turn blue when an aluminum treatment has been applied in combination with growing the plant in acid soil. *Hydrangea* cultivar 'Hopcorn' has been asexually reproduced repeatedly by vegetative cuttings in Huissen, The Netherlands over a five-year period. 'Hopcorn' has been found to retain its distinctive characteristics through successive asexual propagations.

DESCRIPTION OF PHOTOGRAPHS

This new *hydrangea* plant is illustrated by the accompanying photographs which show blooms, buds, and foliage of the plant; the colors shown are as true as can be reasonably obtained by conventional photographic procedures. The photographs are of a three-year old plant grown in a greenhouse.

DESCRIPTION OF THE NEW CULTIVAR

Figure 1:
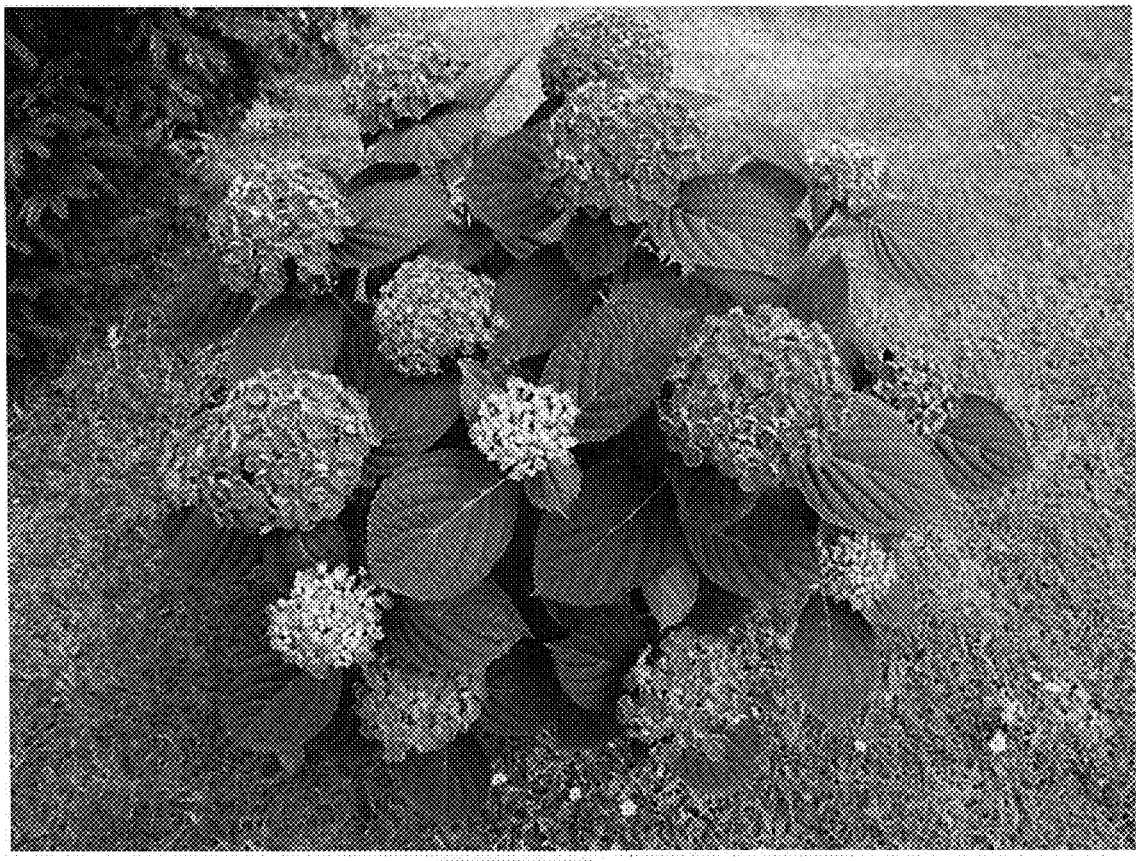
FIG. 1 shows overall plant habit, including blooms and foliage.
Figure 2:
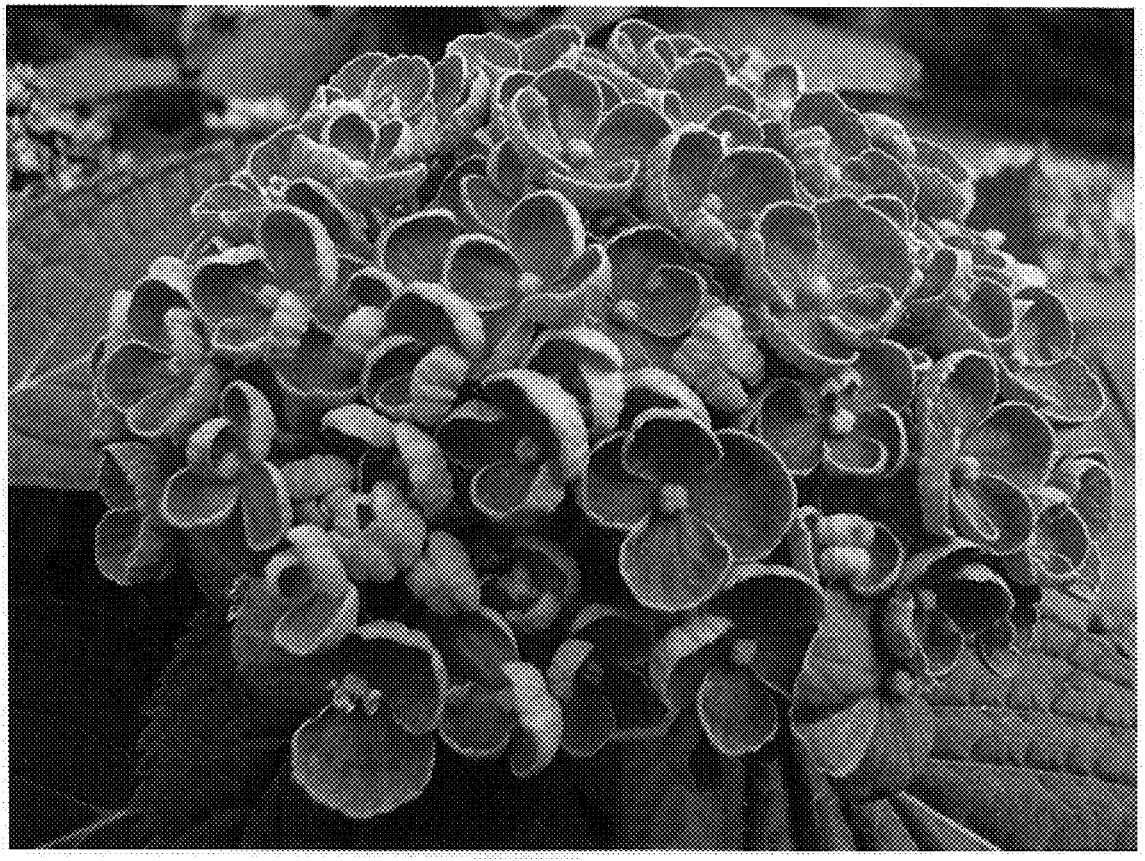
FIG. 2 shows a close-up of a mature inflorescence.

The following detailed description set forth the distinctive characteristics of 'Hopcorn'. The data which define these characteristics were collected from asexual reproductions carried out in Huissen, The Netherlands. The plant history was taken on eighteen-month-old plants grown in three-liter pots, two cuttings per pot, in a greenhouse. Color references are primarily to the R.H.S. Colour Chart of The Royal Horticultural Society of London (R.H.S.) (2001).

DETAILED BOTANICAL DESCRIPTION

Classification:
- *Botanical.*—*Hydrangea macrophylla.*
- *Common name.*—*Hydrangea.*

Parentage: Naturally occurring mutation of *hydrangea* cultivar 'Mathilde Gutges'.

Growth:
- *Habit.*—Medium to tall growth habit; growth retarders are used to keep plants shorter; average sturdiness; 10 to 12 branches with flowers.
- *Height.*—40 cm to 50 cm.
- *Width.*—35 cm to 45 cm.

Stems:
- *General.*—Stems becomes woody as they age.
- *Young stems.*—Color: RHS 139C. Diameter: 0.4 cm to 0.6 cm. Length: 5 cm to 10 cm after first growing season from spring cuttings. Internode length: Strongly dependent on usage of growth retarders; on a plant of 40 cm height the internode length averages 5.5 cm. Shape: Round. Texture: Glabrous. Pubescence: None. Odor: Not different from other *H. macrophylla*. Pith: Type: Solid. Diameter: 0.35 cm (as measured one-half way from apex to start of one year's growth). Color: RHS 155C and RHS 157D. Lenticels: Number: 15 to 20 per centimeter of stem. Shape: Oblong. Size: Length: 0.05 cm to 0.25 cm. Width: 0.03 cm to 0.05 cm. Color: Near RHS 79B and RHS 86A. Orientation: Vertical in the direction of the length of the stem.
- *Mature stems.*—Color: Thin stems: RHS 177A, RHS 197A, and RHS 200D. Thick stems: Near RHS 201C and RHS 198A. Length: 34 cm to 42 cm after the second growing season. Diameter: Thin stems: 0.4 cm to 0.5 cm. Thick stems: 0.55 cm to 0.65 cm. Exfoliation: Thin stems: 0.1 cm to 0.2 cm cracks in the bark. Thick stems: 0.3 cm to 0.4 cm cracks in the bark.

Leaves:

*Arrangement.*—Opposite.

*Color.*—Young leaves: Upper surface: RHS 137A. Lower surface: RHS 137C and RHS 138A. Mature leaves: Upper surface: RHS 136A. Lower surface: RHS 139B and RHS 138A.

*Mature leaf size.*—Length: 13 cm to 15 cm. Width: 9.5 cm to 10.5 cm.

*Apex.*—Acute.

*Base.*—Cuneate to obtuse.

*Shape.*—Elliptic to obovate.

*Margin.*—Serrulate.

*Texture.*—Upper surface: Glabrous. Lower surface: Very few small hairs on main vein and large side veins.

*Venation.*—10 to 12 large prominent side veins coming from the main vein.

*Vein color.*—Near RHS 138B and RHS 139C.

*Petioles.*—Length: 2.8 cm to 3.8 cm. Diameter: 0.4 cm to 0.5 cm. Color: Near RHS 138B and RHS 139C. Texture: Glabrous. Shape: U-shaped with groove above.

Inflorescence:

*Type.*—Compound corymb, semi-globose.

*Diameter.*—11 cm to 15 cm, rounded.

*Depth* (*height*).—6 cm to 8 cm.

*Number of individual flowers per inflorescence.*—50 to 60 sterile flowers in an 11 cm-sized inflorescence; 110 to 120 sterile flowers in a 15 cm-sized inflorescence.

*Blooming habit.*—Blooms from June through September.

*Color.*—At emergence (end of June): Near RHS 63B and RHS 64C. At full bloom (mid-July): Near RHS 59D, RHS 60C and RHS 61B. At fading (September): RHS 186A.

*Peduncle.*—Color: RHS 143A. Length: 4.0 cm to 5.2 cm. Diameter: 0.3 cm to 0.4 cm at the base of 0.15 cm to 0.2 cm at the point where the pedicel begins.

*Pedicel.*—Color: Near RHS 70C. Length: 2.8 cm to 3.4 cm. Diameter: 0.15 cm.

Petals:

*Petal color* (*at full bloom*).—Upper surface: Near RHS 70D and RHS 75B. Lower surface: Near RHS 64D and RHS 68A.

Sepals:

*Number of sepals.*—4 per sterile flower.

*Size, small sterile flowers.*—Length: 0.9 cm to 1.1 cm. Width: 0.9 cm to 1.1 cm.

*Size, large sterile flowers.*—Length: 1.4 cm to 1.6 cm. Width: 1.4 cm to 1.6 cm.

*Shape.*—Cupped; plants forced into flower very early in the season can have sepals that are more cupped than plants that flower later in the season.

*Apex.*—Round.

*Base.*—Obtuse.

*Margin.*—Round and smooth when grown in a heated greenhouse; obtuse on the upper half of the sepal, lower half no incisions, when grown in a cold greenhouse or outside.

*Texture.*—Glabrous.

*Color* (*at full bloom*).—Upper surface: Near RHS 59D, RHS 60C and RHS 61B. Lower surface: Near RHS 64D and RHS 68A.

Reproductive organs:

*Anther.*—Size: Length: 0.1 cm. Width: 0.1 cm. Depth: 0.05 cm. Color: Near RHS 70D and RHS 75B.

*Filament.*—Color: Near RHS 65B, RHS 63C, and RHS 62B. Size: Length: 0.3 cm. Width: Too thin to measure. Pollen color: Near RHS 155C and RHS 155D.

*Pistil.*—Stigma color: RHS 62C. Style color: RHS 63A and RHS 64B.

*Fruit set.*—None observed.

*Seed.*—None observed.

Disease and insect resistance: 'Hopcorn' is less sensitive than average *H. macrophylla* for *Botrytis* during winter storage.

COMPARISON WITH KNOWN CULTIVARS

Cultivar 'Hopcorn' differs from the mutation parent 'Mathilde Gutges' (unpatented) by having smaller sepals than 'Mathilde Gutges' and by having each sepal cupped while 'Mathilde Gutges' has the normal flat sepals.

Cultivar 'Hopcorn' differs from the commercial variety, 'Uzu' (unpatented) by having darker leaves and darker pink flowers. Additionally, 'Hopcorn' also grows more compactly than 'Uzu'.

I claim:

1. A new and distinct cultivar of *hydrangea* plant as shown and described herein.

* * * * *